(12) United States Patent
Dumargue et al.

(10) Patent No.: US 7,579,607 B2
(45) Date of Patent: Aug. 25, 2009

(54) INSTALLATION FOR STERILIZING ARTICLES BY ELECTRON BOMBARDMENT

(75) Inventors: Guy Dumargue, Cherre (FR); Bertrand Gruson, Breville sur Mer (FR); Delphine Raynaud, La Ferte Bernard (FR)

(73) Assignee: Serac Group, La Ferte Brenard (FR)

( * ) Notice: Subject to any disclaimer, the term of this patent is extended or adjusted under 35 U.S.C. 154(b) by 541 days.

(21) Appl. No.: 11/037,263

(22) Filed: Jan. 19, 2005

(65) Prior Publication Data

US 2005/0158218 A1  Jul. 21, 2005

(30) Foreign Application Priority Data

Jan. 20, 2004  (FR) .................................. 04 00473

(51) Int. Cl.
*A61L 2/20* (2006.01)
*A23L 3/26* (2006.01)
*B65B 55/16* (2006.01)
*H05B 6/80* (2006.01)

(52) U.S. Cl. .............................. 250/492.3; 250/453.11; 250/455.11; 422/22; 422/300

(58) Field of Classification Search ............ 219/121.12, 219/121.21, 121.25; 250/492.1, 492.3, 453.11, 250/455.11; 427/457, 566; 156/345.43; 422/121, 186, 22, 24, 21, 300; 118/629–635; 414/150, 151; 204/157.15
See application file for complete search history.

(56) References Cited

U.S. PATENT DOCUMENTS

| | | | | |
|---|---|---|---|---|
| 1,062,379 A * | 5/1913 | Anderson et al. | ........... | 198/442 |
| 3,564,998 A * | 2/1971 | Johnson et al. | ............... | 101/40 |
| 3,731,788 A * | 5/1973 | Delecroix | .................. | 198/576 |
| 3,773,190 A * | 11/1973 | Ishida et al. | ........... | 414/331.06 |
| 3,780,308 A * | 12/1973 | Nablo | ...................... | 250/492.3 |
| 3,833,814 A * | 9/1974 | Nablo | ...................... | 250/492.1 |
| 3,945,796 A * | 3/1976 | Nagamatsu et al. | ......... | 422/296 |
| 4,100,450 A * | 7/1978 | Frutiger et al. | ........... | 313/360.1 |
| 4,891,241 A * | 1/1990 | Hashimoto et al. | .......... | 427/520 |
| 4,944,132 A * | 7/1990 | Carlsson et al. | ............... | 53/167 |
| 5,053,196 A * | 10/1991 | Ide et al. | ........................ | 422/28 |
| 5,154,604 A * | 10/1992 | Arai | ............................ | 432/59 |
| 5,201,994 A * | 4/1993 | Nonaka et al. | ................ | 216/69 |
| 5,204,534 A * | 4/1993 | Dubuit | .................... | 250/492.1 |
| 5,399,198 A * | 3/1995 | Ghaisas | ...................... | 118/629 |
| 5,847,401 A * | 12/1998 | McKeown et al. | .... | 250/396 ML |
| 6,165,526 A * | 12/2000 | Newman | ..................... | 426/248 |
| 6,191,424 B1 * | 2/2001 | Stirling et al. | ......... | 250/455.11 |
| 6,364,518 B1 * | 4/2002 | Gleich et al. | .................. | 366/86 |
| 6,459,089 B1 * | 10/2002 | Masefield et al. | ...... | 250/453.11 |

(Continued)

FOREIGN PATENT DOCUMENTS

DE     2003440 A  *  3/1979

(Continued)

*Primary Examiner*—Samuel M Heinrich
(74) *Attorney, Agent, or Firm*—Muncy, Geissler, Olds & Lowe, PLLC

(57) ABSTRACT

An installation for sterilizing articles comprises an enclosure having an inlet opening and an outlet opening, a support device for moving the articles inside the enclosure, and two electron bombardment members disposed on different orientations relative to the articles to be sterilized and inclined relative to the longitudinal axis of the articles.

13 Claims, 2 Drawing Sheets

U.S. PATENT DOCUMENTS

| | | | |
|---|---|---|---|
| 6,559,610 B2 * | 5/2003 | Tanaka | 315/506 |
| 6,756,597 B2 * | 6/2004 | Avnery et al. | 250/433 |
| 6,833,551 B2 * | 12/2004 | Avnery | 250/492.3 |
| 7,145,155 B2 * | 12/2006 | Nablo et al. | 250/492.1 |
| 7,282,726 B2 * | 10/2007 | Usami et al. | 250/492.3 |
| 2002/0114728 A1 * | 8/2002 | Kulish et al. | 422/22 |
| 2002/0149321 A1 * | 10/2002 | Avnery | 315/169.3 |
| 2005/0092921 A1 * | 5/2005 | Nakasuji et al. | 250/306 |
| 2007/0145304 A1 * | 6/2007 | Roche et al. | 250/493.1 |

FOREIGN PATENT DOCUMENTS

| | | | |
|---|---|---|---|
| DE | 3623250 A | * | 1/1988 |
| FR | 2 838 403 | | 10/2003 |
| JP | 52027471 A | * | 3/1977 |
| JP | 411100009 A | * | 4/1999 |
| JP | 2000203534 A | * | 7/2000 |
| JP | 02000325440 A | * | 11/2000 |
| JP | 2003161800 A | * | 6/2003 |
| WO | WO-98/42385 A1 | | 10/1998 |

* cited by examiner

INSTALLATION FOR STERILIZING ARTICLES BY ELECTRON BOMBARDMENT

The present invention relates to an installation for sterilizing articles, and more particularly but not exclusively for sterilizing bottles.

BACKGROUND OF THE INVENTION

Installations for sterilizing articles, in particular trays for food products, are known, such an installation comprising an enclosure with a conveyor passing therethrough having the articles disposed thereon, and an electron bombardment device disposed above the conveyor for treating the articles with vertical radiation. Such installations are satisfactory for articles of small height, and they enable articles to be sterilized while using low-energy electron radiation.

In contrast, when the articles are of considerable height and/or thickness, for example when the articles are bottles, it is necessary to increase the electron bombardment energy very considerably so that the electron radiation can reach the bottoms of the bottles after passing through their walls and still have enough energy to ensure sterilization at the bottoms of the receptacles. With bottles, the electron bombardment energy also needs to be increased because the neck of the bottle absorbs a fraction of the electron radiation energy before it reaches the bottom of the bottle. High-power electron bombardment then raises the problem of deteriorating the portions of the article that are closest to the bombardment device, in particular the neck when the article is a bottle.

It is also known from document U.S. Pat. No. 4,944,132 a sterilization installation comprising two electron bombardment members disposed at different orientations relative to the articles that are to be sterilized but both emitting a horizontal radiation over receptacles extending vertically. The bottom of a bottle would not be satisfactorily sterilized with an installation according to this document.

In addition, high-power electron bombardment runs the risk of propagating outside the enclosure and thus of constituting a danger for operators moving around the installation.

OBJECT OF THE INVENTION

A main object of the invention is to provide an installation for sterilizing articles that enables the articles to be sterilized sufficiently both internally and externally by means of electron bombardment, and while minimizing deterioration of an article due to the electron bombardment.

Other aspects of the invention seek to minimize the propagation of electron radiation outside the enclosure, and to minimize the penetration of pollution into the inside of the enclosure.

BRIEF DESCRIPTION OF THE INVENTION

In order to achieve the main object of the invention, the invention provides an installation for sterilizing articles, the installation comprising an enclosure having an inlet opening and an outlet opening, a support device for moving the articles inside the enclosure with a vertically extending longitudinal axis, and at least two electron bombardment members disposed at different orientations relative to the articles that are to be sterilized to process the articles as they move through the enclosure, wherein the electron bombardment members are inclined relative to a longitudinal axis of the articles.

Thus, by appropriately positioning the electron bombardment members as a function of the shape of the article to be sterilized, it is possible to ensure that the electron bombardment member is facing a portion of the article that is of small thickness, thus making it possible to ensure that all portions of the article are sterilized, while using electron bombardment at low energy. This enables a complete sterilization of the article, including the bottom of a receptacle, without deterioration of the article.

In another aspect of the invention, the support device comprises at least two support members disposed to support the receptacles in various positions corresponding to respective electron bombardment members, and preferably, the support members are rotary platforms disposed to cause the articles to follow an S-shaped path. This ensures that the support members do not form obstacles to propagation of the radiation while an article is passing in front of the corresponding electron bombardment member.

In yet another advantageous aspect of the invention, the enclosure has side walls presenting a curvilinear or zigzag profile. This ensures that the electron radiation is subjected to a large number of reflections on the walls of the enclosure before reaching the inlet opening or the outlet opening, such that the radiation escaping from the enclosure has residual energy that is low enough to constitute no danger for operators moving around the installation.

According to yet other advantageous aspects of the invention, the enclosure includes wall elements disposed to minimize the flow of air inside the enclosure, and the installation includes a device for injecting a sterile gas into the inside of the enclosure, preferably disposed vertically above the articles. This simultaneously minimizes the amount of polluted air that penetrates from outside the enclosure and the amount of electron radiation that is emitted outside from the enclosure.

BRIEF DESCRIPTION OF THE DRAWINGS

Other characteristics and advantages of the invention will appear on reading the following description of a preferred, non-limiting embodiment of the invention given with reference to the accompanying figures, in which.

DETAILED DESCRIPTION OF THE INVENTION

Figure 1:
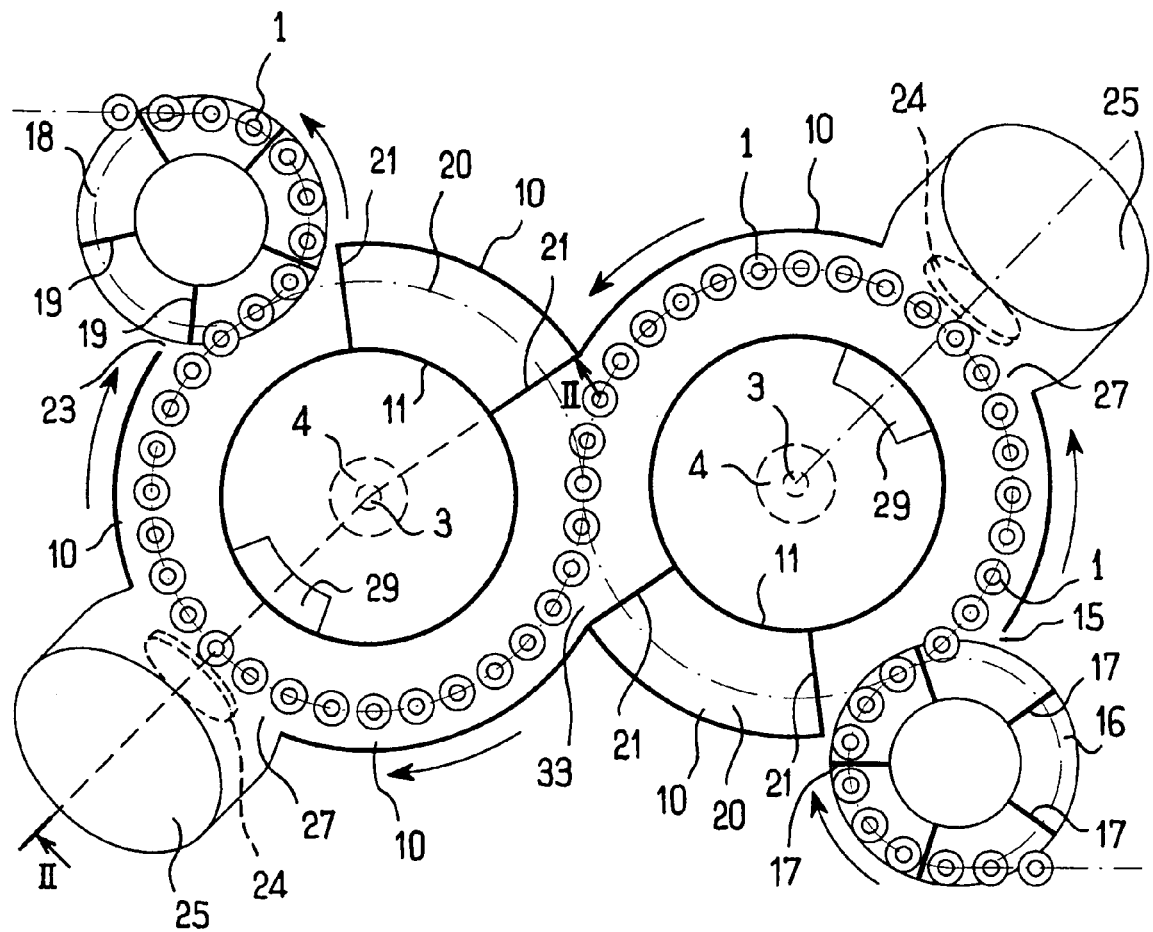
FIG. 1 is a diagrammatic plan view of an installation of the invention.

The invention is described below with reference to an installation for sterilizing bottles 1.

In the embodiment shown, the installation has two bottle-support members comprising in conventional manner a rotary platform 2 (not shown in FIG. 1) supported by a shaft 3 driven in rotation by a motor 4 carried by a frame 5. The rotary platform 2 includes, in likewise conventional manner, grips 6 suitable for taking hold of the bottles 1 around a portion of the neck of each bottle, while leaving the neck uncovered towards the outside of the platform.

The rotary platforms 2 are disposed adjacent to each other and are driven to rotate in opposite directions. The grips 6 are also controlled in conventional manner by a control member (not shown) enabling the bottles to be transferred from one rotary platform to the other as they pass through the point where the rotary platforms are tangential to each other, so that the bottles follow an S-shaped path, as shown in FIG. 1.

An enclosure 7 extends around the support members and defines a volume around the receptacles that enables the receptacles to travel inside the enclosure while they are being carried by the grips 6.

Figure 2:
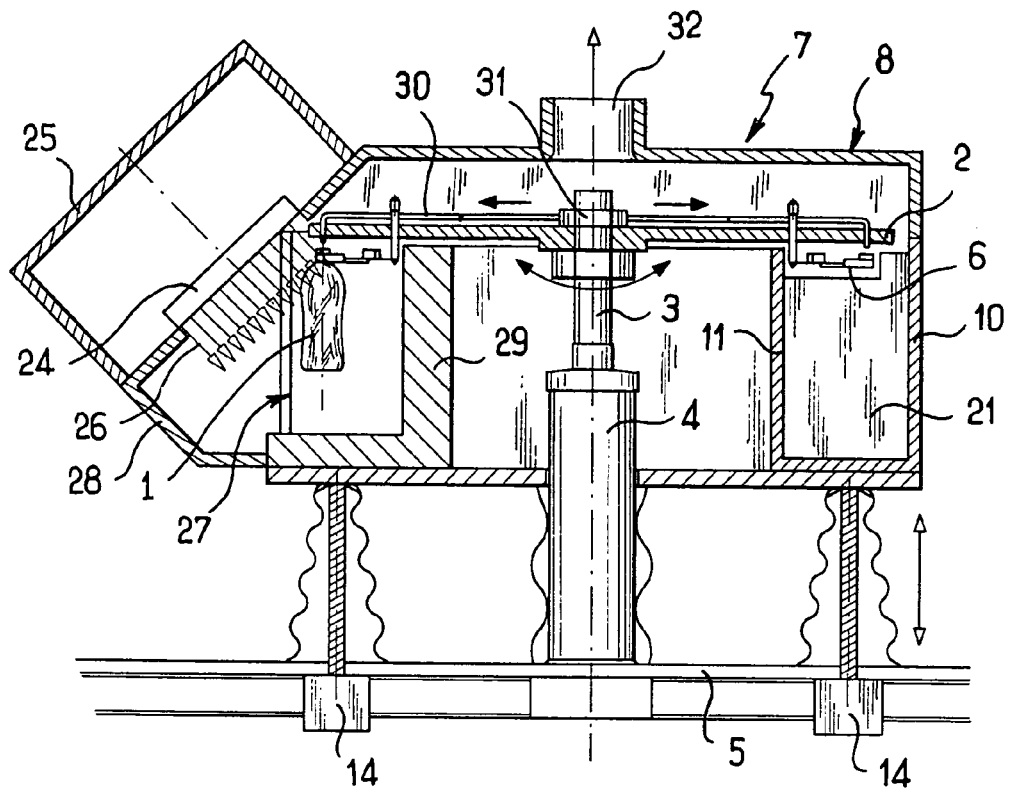
FIG. 2 is a diagrammatic section view on line II-II of FIG. 1 showing the installation in an operating position.
Figure 3:
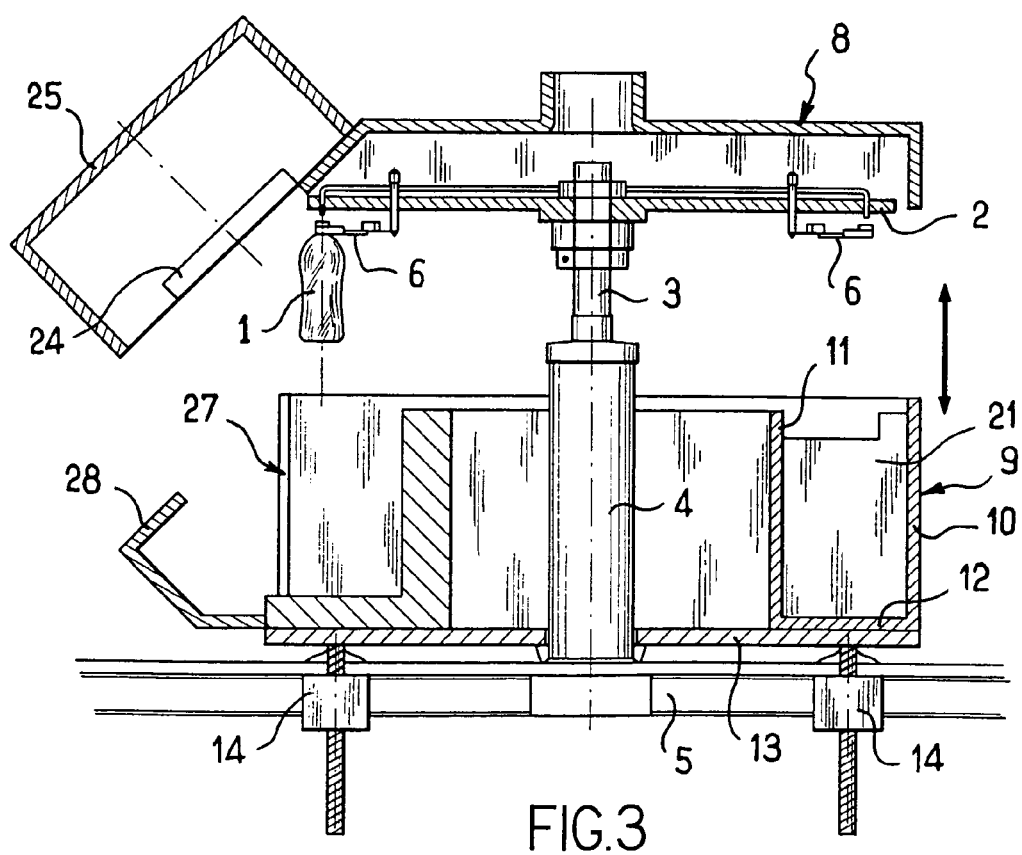
FIG. 3 is a section view analogous to that of FIG. 2 showing the installation in an intervention position.

As shown, the enclosure 7 preferably comprises a cover 8 secured to the frame of the installation by means that are not shown, and a vessel 9 that comprises a cylindrical outer side wall 10 associated with each rotary platform 2 together with a cylindrical inner side wall 11 connected to a bottom wall 12. On either side of the point where the rotary platforms 2 are tangential, the outer side walls 10 are interrupted and are united with one another in leaktight manner so as to define a connection opening 33 between the two portions of the enclosure, each portion being associated with a respective rotary platform 2. The vessel 9 is carried by a vertically movable plate 13 connected to the frame 5 via screw actuators 14 enabling the vessel to be moved between an open position shown in FIG. 3 in which the vessel 9 is in a low position giving access to the grips 6 and to the platforms 2, and an operating position as shown in FIG. 2 in which the outer wall 10 of the vessel is in radiation-tight contact with the cover 8, for example by using a baffle gasket, and the inner side wall 11 has a top edge extending under the platform 2 in the vicinity thereof so as to allow the platform 2 to turn without friction, while also providing a screen to the electron radiation that is described below. The enclosure is preferably made of steel with an inner lining of lead.

The outer wall 10 of the enclosure is pierced by an inlet opening 15 facing a bottle insertion rotary device 16, e.g. a transfer star, having radial partitions 17 that are spaced apart by a distance that is small enough to ensure that two radial partitions 17 are continuously adjacent to the edges of the opening 15. The radial partitions 17 thus minimize a risk of polluted outside air penetrating into the inside of the enclosure, and they also constitute obstacles to any of the electron radiation that is being reflected inside the enclosure managing to leak out. In an opposite zone of the enclosure, the installation includes a rotary device 18 for extracting bottles from the enclosure. The rotary extractor device 18 faces an outlet opening 23 formed in the outer side wall 10 of the enclosure. Like the rotary device 16, the rotary device 18 includes radial partitions 19 forming obstacles to outside air penetrating into the inside of the enclosure. In addition, at the ends of dead zones 20 in which the grips 6 do not carry any bottles, the vessel has radial partitions 21 that are cut so as to allow a platform 2 to rotate together with the associated grips 6 while minimizing any risk of polluted external air penetrating via the corresponding dead zone 20.

In two zones that are radially opposite relative to the path of the bottles 1, the installation has two electron bombardment members 24, each disposed in a housing 25 that is secured to the cover 8 in order to emit electron radiation 26 at 45° relative to the vertical longitudinal axes of the bottles 1. The electron radiation 26 penetrates into the enclosure 7 via an opening 27 in the outer side wall 10 of the enclosure. Like the enclosure, the housing 25 is preferably made with an inner lining of lead. In order to ensure continuity between the housing 25 and the vessel of the enclosure, the enclosure includes a casing element 28 of appropriate shape that is secured to the vessel 9. Facing the terminal member 24, the inner wall 1 of the vessel 9 is preferably reinforced by a piece of lead 29 that absorbs direct electron radiation so as to prevent it from propagating through the inner side wall of the enclosure.

Furthermore, an injector pipe 30 is associated with each grip 6. Each injector pipe 30 has one end opening out vertically above a bottle 1, and an opposite end connected to a rotary joint 31 enabling the injector pipe 30 to be fed with a sterile gas under pressure from a gas source that is not shown. The sterile gas is preferably nitrogen, thereby enabling ozone production during electron bombardment to be reduced. The sterile gas under pressure also raises the pressure inside the enclosure 7 so as to minimize any penetration of external air. In order to ensure that the pressure inside the enclosure does not become too great, the cover 8 is preferably fitted with an extractor orifice 32.

Naturally, the invention is not restricted to the embodiment shown and can be the subject of variants in implementation without going beyond the ambit of the invention as defined by the claims.

In particular, although the sterilization installation is described as being for sterilizing bottles, it could be used for sterilizing any kind of article, the articles being supported by an appropriate support device. Although the sterilization installation of the invention is shown as having two electron bombardment members associated with two rotary support members, the number of electron bombardment members should be adapted to the shape and the size of the articles in order to achieve the desired sterilization, while minimizing the number of electron bombardment members. It is also possible to associate a plurality of electron bombardment members with a single support member if the configuration of the support member and the shape of the articles for sterilization make that possible.

Although the enclosure of the invention is described as having side walls that are cylindrical, it would be possible to use an enclosure having side walls of curvilinear or zigzag profile so as to ensure that the electron radiation is subjected to successive reflections on the walls of the enclosure, thereby reducing the intensity of the radiation before it reaches the inlet orifice or the outlet orifice of the enclosure.

Although the invention is described with reference to electron bombardment means emitting radiation at 45°, the value of this angle of inclination within the range from 0° to 90° with respect to the vertical direction of the longitudinal axes of the articles should be adapted to the shape of the articles to be sterilized and to their wall thickness when the articles are receptacles.

What is claimed is:

1. An installation for sterilizing articles, the installation comprising an enclosure having an inlet opening and an outlet opening, a support device for moving the articles inside the enclosure in such a way that each article has a vertically extending longitudinal axis, and at least two electron bombardment members disposed to emit beams of radiation that are inclined at different orientations relative to the longitudinal axis of the articles that are to be sterilized to process the articles as they move through the enclosure, the support device comprising at least two support members disposed to support the articles in various positions corresponding to respective electron bombardment members and the support members being rotary platforms disposed to cause the articles to follow an S-shaped path.

2. The installation according to claim 1, wherein each of said orientations includes an inclined angle between 0 and 90 degrees to vertical.

3. The installation according to claim 2, wherein the inclined angle is about 45 degrees.

4. An installation according to claim 1, wherein the enclosure has side walls presenting a curvilinear or zigzag profile.

5. An installation according to claim 1, wherein the support device comprises at least one rotary platform for supporting the articles, and wherein the enclosure has cylindrical side walls between which the articles move.

6. An installation according to claim 5, wherein the enclosure includes a dead zone closed by radial partitions.

7. An installation according to claim 5, including rotary devices for introducing articles and for extracting articles, the rotary devices including radial partitions.

8. An installation according to claim 1, wherein the enclosure comprises at least two portions that are movable relative to each other in order to provide access to the articles.

9. An installation according to claim 1, including a device for injecting sterile gas into the inside of the enclosure.

10. An installation according to claim 9, wherein the device for injecting sterile gas comprises injection pipes each having one end extending vertically above the articles.

11. The installation according to claim 1, wherein the articles are a plurality of discrete, separated articles.

12. An installation for sterilizing articles, comprising:
an enclosure having an inlet opening and an outlet opening;
a support device for moving said articles within said enclosure, including two rotary platforms moving in opposite directions and adjacent each other at one point;
said articles being moved with the longitudinal axis extending in the vertical direction along a path following a curve along an outer edge of one of said rotary platforms to said point and then following a curve in the opposite direction along an outer edge of the other of said rotary platforms to form an S-shaped path; and
two electron bombardment members emitting electrons at an inclined angle to vertical at said path so as to sterilize said articles moving thereon, one of said electron bombardment members being placed along the path on each of said two rotary platforms, so that opposite sides of said articles are bombarded by each electron bombardment member.

13. The installation according to claim 12, wherein said inclined angle is about 45 degrees.

* * * * *